US012562253B2

(12) United States Patent
Hammer et al.

(10) Patent No.: US 12,562,253 B2
(45) Date of Patent: *Feb. 24, 2026

(54) SOFT TISSUE MATERIAL CUMULATIVE DAMAGE MODEL FOR REDUCING REPETITIVE STRESS INJURIES IN PERFORMING A PROCESS

(71) Applicant: The Boeing Company, Chicago, IL (US)

(72) Inventors: Liisa Charlie Hammer, Seattle, WA (US); James Dean Cotton, Issaquah, WA (US); Richard Jay Gardner, Brier, WA (US); Karen Chiyono Takatani, Renton, WA (US)

(73) Assignee: THE BOEING COMPANY, Arlington, VA (US)

( * ) Notice: Subject to any disclaimer, the term of this patent is extended or adjusted under 35 U.S.C. 154(b) by 662 days.

This patent is subject to a terminal disclaimer.

(21) Appl. No.: 17/110,953

(22) Filed: Dec. 3, 2020

(65) Prior Publication Data

US 2021/0174929 A1     Jun. 10, 2021

Related U.S. Application Data

(60) Provisional application No. 62/944,799, filed on Dec. 6, 2019.

(51) Int. Cl.
| | |
|---|---|
| *G16H 20/30* | (2018.01) |
| *G16H 50/30* | (2018.01) |
| *G16H 50/70* | (2018.01) |

(52) U.S. Cl.
CPC ............. *G16H 20/30* (2018.01); *G16H 50/30* (2018.01); *G16H 50/70* (2018.01)

(58) Field of Classification Search
None
See application file for complete search history.

(56) References Cited

U.S. PATENT DOCUMENTS

| | | | |
|---|---|---|---|
| 9,610,036 | B1 | 4/2017 | De Sapio et al. |
| 2003/0135129 | A1 | 7/2003 | Cusimano et al. |

(Continued)

FOREIGN PATENT DOCUMENTS

| | | |
|---|---|---|
| EP | 2839772 A1 | 2/2015 |
| JP | 2011141706 A | 7/2011 |

(Continued)

OTHER PUBLICATIONS

Fung, D.T., Wang, V.M., Laudier, D.M., Shine, J.H., Basta-Pljakic, J., Jepsen, K.J., Schaffler, M.B. and Flatow, E.L., 2009. Subrupture tendon fatigue damage. Journal of Orthopaedic Research, vol. 27(2), pp. 264-273. (Year: 2009).*

(Continued)

*Primary Examiner* — G. Steven Vanni
*Assistant Examiner* — Meredith Abbott Vassell
(74) *Attorney, Agent, or Firm* — MH2 Technology Law Group LLP

(57) ABSTRACT

Techniques for reducing repetitive stress injuries to soft tissue in performing a process are disclosed. The techniques include obtaining at least one repetitive stress data set related to the soft tissue and to the process; accessing information characterizing a first damage regime and second information characterizing a second damage regime, where the first information quantifies a number of repetitions at a given stress for the soft tissue to transition out of the first damage regime, and wherein the second information quantifies a number of repetitions at a given stress for the soft tissue to transition out of the second damage regime; predicting conditions sufficient for damage to the soft tissue;

(Continued)

determining, based on at least the predicting, at least one guideline for reducing a risk of a soft tissue material repetitive stress injury; and implementing the at least one guideline in the process.

19 Claims, 5 Drawing Sheets

(56)                    References Cited

U.S. PATENT DOCUMENTS

| | | |
|---|---|---|
| 2017/0055836 A1 | 3/2017 | Thelen et al. |
| 2022/0192637 A1 | 6/2022 | Kirby et al. |
| 2022/0230732 A1 | 7/2022 | Hammer et al. |
| 2022/0338928 A1 | 10/2022 | Hammer et al. |
| 2023/0067316 A1 | 3/2023 | Hammer et al. |

FOREIGN PATENT DOCUMENTS

| | | |
|---|---|---|
| WO | 2014201020 A1 | 12/2014 |
| WO | 2021113725 A1 | 6/2021 |

OTHER PUBLICATIONS

Takatani et al. 2017 A new approach to prevent overuse injuries of the rotator cuff supraspinatus tendon using the cumulative fatigue concept. Theoretical Issues in Ergonomics Science, vol. 18(5), pp. 455-475. (Year: 2017).*

Buckley et al.. 2013. Validation of an empirical damage model for aging and in vivo injury of the murine patellar tendon. Journal of biomechanical engineering, vol. 135(4), pp. 041005-1-041005-7. (Year: 2013).*

Colombini, D. and Occhipinti, E., 2006. Preventing upper limb work-related musculoskeletal disorders (UL-WMSDS): New approaches in job (re) design and current trends in standardization. Applied ergonomics, vol. 37(4), pp. 441-450. (Year: 2006).*

Van Eerd et al. 2016. Effectiveness of workplace interventions in the prevention of upper extremity musculoskeletal disorders and symptoms: an update of the evidence. Occupational and Environmental Medicine, vol. 73(1), pp. 62-70. (Year: 2016).*

Daneshmandi, H., Kee, D., Kamalinia, M., Oliaei, M. and Mohammadi, H., 2018. An ergonomic intervention to relieve musculoskeletal symptoms of assembly line workers at an electronic parts manufacturer in Iran. Work, 61(4), pp. 515-521. (Year: 2018).*

Garg, A. and Kapellusch, J.M., 2009. Applications of biomechanics for prevention of work-related musculoskeletal disorders. Ergonomics, 52(1), pp. 36-59. (Year: 2009).*

Notification Concerning Transmittal of International Preliminary Report on Patentability mailed Jun. 16, 2022 In corresponding International Application No. PCT/US2020/063430, 8 pages.

Golze, Doreen (PCT Authorized officer), Notification of Transmittal of the International Search Report and the Written Opinion of the International Searching Authority, or the Declaration, mailed Mar. 26, 2021, 15 pages.

Qasim et al., "Initiation and Progression of Mechanical Damage in the Intervertebral Disc Under Cyclic Loading Using Continuum Damage Mechanics Methodoloty: A Finite Element Study," Journal of Biomechanics 45 (2012) 1934-1940.

Extended European Search Report for European Application No. 21215965.1 dated Jun. 8, 2022 (11 pages).

De Sapio, V., et al., "Demographic Specific Musculoskeletal Models of Factory Worker Performance, Fatigue, and Injury," 2016 IEEE Aerospace Conference, IEEE, Mar. 5, 2016, pp. 1-13.

Kim, Y.-S., et al., "In Vivo Strain Analysis of the Intact Supraspinatus Tendon by Ultrasound Speckles Tracking Imaging," Journal of Orthopaedic Research, Dec. 2011, 29(12): 1931-1937.

Klauser, A.S., et al., "Sonoelastography: Musculoskeletal Applications," Radiology, Sep. 2014, 272(3):622-633.

Lake, S.P., et al., "Effect of Fiber Distribution and Realignment on the Nonlinear and Inhomogeneous Mechanical Properties of Human Supraspinatus Tendon Under Longitudinal Tensile Loading," NIH Public Access Author Manuscript, J. Orthop. Res., Dec. 2009, 27(12): 1596 (17 pages).

Prado-Costa, R., et al., "Ultrasound elastography: compression elastography and shear-wave elastography in the assessment of tendon injury," Insights into Imaging, 2018 (Published online Aug. 17, 2018), 9: 791-814.

Rabello, L.M., et al., "Substantiating the Use of Ultrasound Tissue Characterization in the Analysis of Tendon Structure: A Systematic Review," www.cjsportmed.com, Clin. J. Sport Med., May 2021, 31(3):e161-e175.

Schechtman, H., et al., "In Vitro Fatigue of Human Tendons," J. Biomechanics, Aug. 1997, 30(8):829-835.

Van Schie, H.T.M., et al., "Efficacy of computerized discrimination between structure-related and non-structure-related echoes in ultrasonographic images for the quantitative evaluation of the structural integrity of superficial digital flexor tendons in horses," Am. J. Vet. Res., Jul. 2001, 62(7):1159-1166.

Van Schie, H.T.M., et al., "Ultrasonographic Tissue Characterisation of Human Achilles Tendons: Quantification of Tendon Structure Through a Novel Non-Invasive Approach," Br. J. Sports Med., Dec. 2010 (Published online Aug. 6, 2009), 44(16):1153-11599.

Crisan, Carmen-Clara (PCT Authorized Officer), Notification of Transmittal of the International Search Report and the Written Opinion of the International Searching Authority, or the Declaration, mailed Jul. 19, 2022, for International Application No. PCT/US2022/022473, 22 pages.

Huber, G., et al., "Dependence of spinal segment mechanics on age and posture," Research Project F 2069—Bundesanstalt für Arbeitsschutz und Arbeitsmedizin, May 3, 2010, pp. 1-173.

Qasim, M., et al., "Initiation and progression of mechanical damage in the intervertebral disc under cyclic loading using continuum damage mechanics methodology: A finite element study," Journal of Biomechanics, vol. 45, No. 11, Jul. 26, 2012 (Published online Jun. 8, 2012), pp. 1934-1940.

Weiss, J.A., et al., "Three-dimensional finite element modeling of ligaments: Technical aspects," Medical Engineering & Physics, vol. 27, No. 10, Aug. 8, 2005, pp. 845-861.

Zhang, Q., et al., "Techniques for In Vivo Measurement of Ligament and Tendon Strain: A Review," Annals of Biomedical Engineering, vol. 49, No. 1, Jan. 2021 (Published online Oct. 6, 2020), pp. 7-28.

Tse, K.M., et al., "A review of head injury and finite element head models," American Journal of Engineering, Technology and Society, vol. 1, No. 5, Dec. 2014, pp. 28-52.

Doherty, F. (PCT Authorized Officer), Notification Concerning Transmittal of International Preliminary Report on Patentability and Written Opinion of the International Searching Authority mailed Nov. 9, 2023, for International Application No. PCT/US2022/022473, 15 pages.

Office Action mailed in CA 3,158,278 on Feb. 19, 2024. (5 Pages).

Office Action issued on Jun. 25, 2024, for Japanese Application No. 2022-534139, including English machine translation, 8 pages.

Examination Report No. 1 for Standard Patent Application, issued Jun. 13, 2025 in corresponding Australian Patent No. 202039817, 4 pages.

Edwards, W. Brent, "Modeling Overuse Injuries in Sport as a Mechanical Fatigue Phenomenon," Exercise and Sport Sciences Reviews, vol. 46, No. 4, Oct. 2018, pp. 224-231.

Murakami, Y., et al., "Essential structure of S-N curve: Prediction of fatigue life and fatigue limit of defective materials and nature of scatter," International Journal of Fatigue, vol. 146, Article 106138, 2021 (Available online Jan. 5, 2021), 14 pages.

Pizzolato, C., et al., "Bioinspired Technologies to Connect Musculoskeletal Mechanobiology to the Person for Training and Rehabilitation," Frontiers in Computational Neuroscience, vol. 11, Article 96, Oct. 18, 2017, pp. 1-16.

* cited by examiner

100

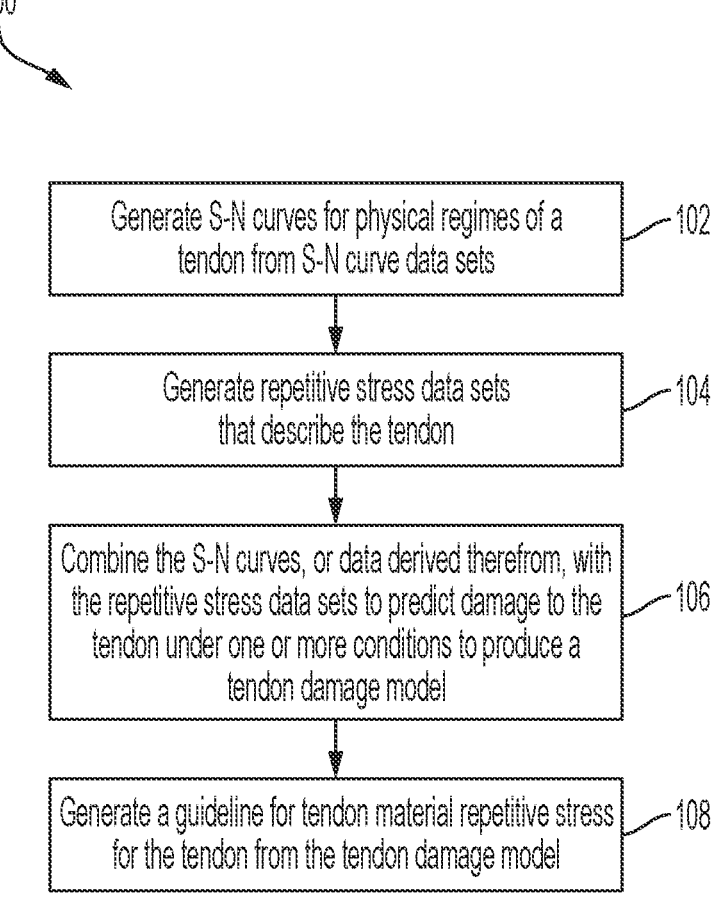

| Generate S-N curves for physical regimes of a tendon from S-N curve data sets | 102 |

| Generate repetitive stress data sets that describe the tendon | 104 |

| Combine the S-N curves, or data derived therefrom, with the repetitive stress data sets to predict damage to the tendon under one or more conditions to produce a tendon damage model | 106 |

| Generate a guideline for tendon material repetitive stress for the tendon from the tendon damage model | 108 |

Obtain Repetitive Stress Data Set — 402

Access Information
Characterizing Damage Regimes — 404

Predict Conditions Sufficient for
Damage to the Soft Tissue — 406

Determine Guideline — 408

Implement Guideline — 410

SOFT TISSUE MATERIAL CUMULATIVE DAMAGE MODEL FOR REDUCING REPETITIVE STRESS INJURIES IN PERFORMING A PROCESS

RELATED APPLICATION

The present application claims priority to, and the benefit of, U.S. Provisional Patent Application No. 62/944,799, filed Dec. 6, 2019, entitled "Systems and Methods for Developing a Tendon Material Cumulative Damage Model, which is hereby incorporated by reference in its entirety.

FIELD

The subject matter described herein generally relates to the field of material science and its application to ergonomics. More particularly, the subject matter disclosed herein relates to soft tissue material repetitive stress injuries and guidelines to minimize the risk of sustaining such injuries.

BACKGROUND

Overuse injuries, particularly of the shoulder, including the supraspinatus tendon, are some of the most significant of ergonomics injuries. Accordingly, there is a need to understand the dynamics of workplace or other activities that contribute to and can result in stress, for example to a tendon, to address a task or repetition of tasks that contribute to an injury.

To create this understanding, information was drawn from several fields of research including medical equipment, surgical techniques, medicine, engineering, materials science, and ergonomics. Additionally, these fields of research currently do not intersect in a way that a model of material repetitive stress injuries and guidelines can be created easily (or has been developed). This is demonstrated by the body of research and its focus. For example, medical, therapeutic, and pharmacological research is dedicated to (or focuses on) individuals after injury has occurred: surgical procedures, physical therapy regimens, and treatments to speed recovery. Injury detection is focused on after a patient has self-reported an injury, not to screen for risk prior to injury. While traditional ergonomics practices seek to prevent injuries, it has only or so far been done so at the macro level with epidemiological methods: based on estimated work exposure, create an estimate when will a person self-report an injury based on discomfort level or pain, and create guidelines below that threshold and most injuries are defined by generalized body area: the entire shoulder, knee, or back, but not individual components. Engineering publications starting from the 1990s demonstrated ex vivo tendon materials are subject to strength reduction following repetitive stress, consistent with structural fatigue principles. These works did not report on the utility of this information for creating a model, or preventing or predicting injury. Neither did they explore significant structure and property differences between tendon and non-biological structures, nor the need to identify (or develop) engineered materials that could be used as surrogates for further testing, instead of tendon, which is difficult to obtain and subject to changes and degradation once removed from living tissue. A new approach is needed that ties together multidisciplinary research, fills the gaps, and takes advantage of evolving technology in several fields. Significant advances in computer technology make the creation of a materials model more compelling. Computational material models can simulate fatigue behavior of existing or potential new materials. Ultrasonic interrogation can estimate material acoustic properties of biological material within a living subject, and these can be correlated with certain mechanical properties, such as elastic modulus. Motion tracking technology can be used to observe a person in work and simulate those movements within a digital body. These technologies represent an opportunity to develop a model which can generate guidelines to prevent soft tissue injuries in the workplace. The model can also take into account individual characteristics to create a model that is personalized. A working model can also be used in reverse: to inform design requirements for building artificial or replacement tendons and how those tendons would perform in a lifetime of movements.

SUMMARY

The present disclosure is directed to systems and related methods of generating tendon damage models. Typically, these systems and related methods involve generating guidelines for mitigating or minimizing tendon material repetitive injury.

According to various examples, a method of reducing the potential for repetitive stress injuries to soft tissue in performing a process is disclosed. The method includes obtaining at least one repetitive stress data set related to the soft tissue and to the process; accessing at least first information characterizing a first damage regime and second information characterizing a second damage regime, wherein the first information quantifies a number of repetitions at a given stress for the soft tissue to transition out of the first damage regime, and wherein the second information quantifies a number of repetitions at a given stress for the soft tissue to transition out of the second damage regime; predicting, based on at least the first information, the second information, and the repetitive stress data set, conditions sufficient for damage to the soft tissue; determining, based on at least the predicting, at least one guideline for reducing a risk of a soft tissue material repetitive stress injury; and implementing the at least one guideline in the process.

Various optional features of the above examples include the following. The first damage regime and the second damage regime may each include one of: a no damage regime, a sub-rupture damage regime, or a tear propagation regime. The method may include accessing third information characterizing a third damage regime, wherein the third information quantifies a number of repetitions at a given stress for the soft tissue to transition out of the third damage regime; wherein the first damage regime comprises a no damage regime, the second damage regime comprises a sub-rupture damage regime, and the third damage regime comprises a tear propagation regime. The repetitive stress data set may include a force over a cross sectional area of the soft tissue and at least one of a number of repetitions for, or a duration of, at least one task of the process. The obtaining the at least one repetitive stress data set related to the soft tissue and to the process may include estimating at least one stress distribution in the soft tissue. The at least one guideline may include a limitation on at least one of: a posture of the soft tissue, a number of repetitions of a given movement of the soft tissue, a force applied to the soft tissue, a duration of maintaining a given posture of the soft tissue, a duration of a repetition of a given movement of the soft tissue, or a duration of a given force applied to the soft tissue. The accessing at least first information characterizing a first damage regime and second information characterizing a second damage regime may include obtaining at least one of: ultrasound data, computerized axial tomography (CAT) scan data, magnetic resonance imaging (MRI) scan data, destructive testing data, cadaver material data, animal material data, polymer surrogate material data, molecular dynamic modeling (MDM) data, or publication data. The soft tissue may include a teres minor tendon, an infraspinatus tendon, a supraspinatus tendon, a subscapularis tendon, a deltoid tendons, a biceps tendon, a triceps tendon, a brachioradialis tendon, a supinator tendon, a flexor carpi radialis tendon, a flexor carpi ulnaris tendon, an extensor carpi radialis tendon, an extensor carpi radialis brevis tendon, an iliopsoas tendon, an obturator internus tendon, an adductor longus tendon, an adductor brevis tendon, an adductor magnus tendon, a gluteus maximus tendon, a gluteus medius tendon, a quadriceps tendon, a patellar tendon, a hamstring tendon, a sartorius tendon, a gastrocnemius tendon, an Achilles tendon, a soleus tendon, a tibialis anterior tendon, a peroneus longus tendon, a flexor digitorum longus tendon, an interosseus tendon, a flexor digitorum profundus tendon, an abductor digiti minimi tendon, an opponens pollicis tendon, a flexor pollicis longus tendon, an extensor tendon, an abductor pollicis tendon, a flexor hallucis longus tendon, a flexor digitorum brevis tendon, a lumbrical tendon, an abductor hallucis tendon, a flexor digitorum longus tendon, an abductor digiti minimi tendon, an ocular tendon, a levator palpebrae tendon, a masseter tendon, a temporalis tendon, a trapezius tendon, a sternocleidomastoid tendon, a semispinalis capitis tendon, a splenius capitis tendon, a mylohyoid tendon, a thyrohyoid tendon, a sternohyoid tendon, a rectus abdominis tendon, an external oblique tendon, a transversus abdominis tendon, a latissimus dorsi tendon, or an erector spinae tendon. The method may include individualizing the at least one guideline for a subject by applying one or more demographic variables for the subject to the at least one guideline. The method may include obtaining one or more usage data sets for the soft tissue in a subject; and estimating damage to the soft tissue in the subject by comparing the usage data sets to the at least one guideline.

According to various examples, a computer system for reducing repetitive stress injuries to soft tissue in performing a process is disclosed. The system includes at least one electronic processor that executes instructions to perform operations comprising: obtaining at least one repetitive stress data set related to the soft tissue and to the process; accessing at least first information characterizing a first damage regime and second information characterizing a second damage regime, wherein the first information quantifies a number of repetitions at a given stress for the soft tissue to transition out of the first damage regime, and wherein the second information quantifies a number of repetitions at a given stress for the soft tissue to transition out of the second damage regime; predicting, based on at least the first information, the second information, and the repetitive stress data set, conditions sufficient for damage to the soft tissue; and determining, based on at least the predicting, at least one guideline for reducing a risk of a soft tissue material repetitive stress injury; whereby the at least one guideline is implemented in the process.

Various optional features of the above examples include the following. The first damage regime and the second damage regime may each include one of: a no damage regime, a sub-rupture damage regime, or a tear propagation regime. The operations may further comprise: accessing third information characterizing a third damage regime, wherein the third information quantifies a number of repetitions at a given stress for the soft tissue to transition out of the third damage regime; wherein the first damage regime comprises a no damage regime, the second damage regime comprises a sub-rupture damage regime, and the third damage regime comprises a tear propagation regime. The repetitive stress data set may include a force over a cross sectional area of the soft tissue and at least one of a number of repetitions for, or a duration of, at least one task of the process. The obtaining the at least one repetitive stress data set related to the soft tissue and to the process may include estimating at least one stress distribution in the soft tissue. The at least one guideline may include a limitation on at least one of: a posture of the soft tissue, a number of repetitions of a given movement of the soft tissue, a force applied to the soft tissue, a duration of maintaining a given posture of the soft tissue, a duration of a repetition of a given movement of the soft tissue, or a duration of a given force applied to the soft tissue. The accessing at least first information characterizing a first damage regime and second information characterizing a second damage regime may include obtaining at least one of: ultrasound data, computerized axial tomography (CAT) scan data, magnetic resonance imaging (MRI) scan data, destructive testing data, cadaver material data, animal material data, polymer surrogate material data, molecular dynamic modeling (MDM) data, or publication data. The soft tissue may include a teres minor tendon, an infraspinatus tendon, a supraspinatus tendon, a subscapularis tendon, a deltoid tendons, a biceps tendon, a triceps tendon, a brachioradialis tendon, a supinator tendon, a flexor carpi radialis tendon, a flexor carpi ulnaris tendon, an extensor carpi radialis tendon, an extensor carpi radialis brevis tendon, an iliopsoas tendon, an obturator internus tendon, an adductor longus tendon, an adductor brevis tendon, an adductor magnus tendon, a gluteus maximus tendon, a gluteus medius tendon, a quadriceps tendon, a patellar tendon, a hamstring tendon, a sartorius tendon, a gastrocnemius tendon, an Achilles tendon, a soleus tendon, a tibialis anterior tendon, a peroneus longus tendon, a flexor digitorum longus tendon, an interosseus tendon, a flexor digitorum profundus tendon, an abductor digiti minimi tendon, an opponens pollicis tendon, a flexor pollicis longus tendon, an extensor tendon, an abductor pollicis tendon, a flexor hallucis longus tendon, a flexor digitorum brevis tendon, a lumbrical tendon, an abductor hallucis tendon, a flexor digitorum longus tendon, an abductor digiti minimi tendon, an ocular tendon, a levator palpebrae tendon, a masseter tendon, a temporalis tendon, a trapezius tendon, a sternocleidomastoid tendon, a semispinalis capitis tendon, a splenius capitis tendon, a mylohyoid tendon, a thyrohyoid tendon, a sternohyoid tendon, a rectus abdominis tendon, an external oblique tendon, a transversus abdominis tendon, a latissimus dorsi tendon, or an erector spinae tendon. The operations may further include individualizing the at least one guideline for a subject by applying one or more demographic variables for the subject to the at least one guideline. The operations may further include: obtaining one or more usage data sets for the soft tissue in a subject; and estimating damage to the soft tissue in the subject by comparing the usage data sets to the at least one guideline.

In one aspect, the present disclosure provides a method of generating a tendon damage model (e.g., a tendon damage accumulation model, etc.). The method includes generating one or more S-N curves for one or more physical regimes of at least one tendon from one or more S-N curve data sets, wherein a given S-N curve comprises a plot of a magnitude of stress applied to the tendon versus a number of repetitions to failure of the tendon. The method also includes generating one or more repetitive stress data sets that describe the tendon, and combining the S-N curves, or data derived therefrom, with the repetitive stress data sets to predict damage to the tendon under one or more conditions (e.g., physical or tangible representations or information of the tendon damage under a given set of conditions), thereby generating the tendon damage model. It should be noted, however, that the physical mechanism by which damage is accumulated in biological materials, such as collagen-based tendon, is very different from that of traditional crystalline, structural materials, from which the S-N type behavior model was based. The common model for the latter is damage accumulation via dislocation pile-up at glide obstacles in (typically) metallic grains, or crystals. As more cycles are applied, dislocations are generated at discontinuities in the structural material microstructure and gradually pile up against an obstacle, and even though the macroscopic stress is well below the material yield strength, continual cyclic loading will eventually result in a small fissure at the pile-up location. This will then behave as a material defect and eventually grow into a crack. Although prior art approaches have attempted to model fatigue within soft tissue, such attempts produce inaccurate results because they treat soft tissue as if it had the fatigue properties of metal. However, the fatigue and crack mechanism of metals has no true analogue in collagen-based tendons subject to similar cyclic loading, though the S-N type behavior is observed. This is because there are no dislocations accommodating local plastic deformation in tendons. Tendons instead accommodate cyclic loading by localized stretching and kinking of collagen fibers, which can be considered to be a form of micro-damage. Such damage can be repaired by the body by reorganization of the collagen, but it is time-based and subject to healing processes within the body. Hence, an effective model for damage accumulation in tendon structures incorporates: a) a representation of micro-damage accumulation, in advance of a detectable defect (or tear); b) a representation of the healing processes counteracting said micro-damage at a competing rate; c) a representation of the linking up and extension of micro-damage to create a detectable macroscopic defect in the tendon, typically represented as a tear or fissure of the collagen structure and may also be coincident with pain; d) a representation of the extension and growth of this tear or fissure with time (da/dn) if continued cyclic loading is applied above a critical threshold stress intensity, Kc; and, e) a representation of the gross load cycles that result in catastrophic separation or effective failure of the tendon to carry service loads. This latter, e), is the usual mode of S-N fatigue-type data. Model components for each of the above processes will identify four (4) regimes of damage accumulation: 1) no damage; 2) micro-damage (subrupture) accumulation; 3) damage accumulation in the form of a growing tear or fissure, cellular matrix damage or other biological damage; and 4) a state of catastrophic failure or separation of the tendon structure. These model components can be represented mathematically and integrated into a collective model. Such a collective model is also validated by inspection or interrogation methods that can identify the presence and extent of advancing micro-damage and tears.

In another aspect, the present disclosure provides a method of generating a guideline for avoiding tendon material repetitive stress and/or tendon damage accumulation. The method includes generating one or more S-N curves for one or more physical regimes of at least one tendon from one or more S-N curve data sets, wherein a given S-N curve comprises a plot of a magnitude of stress applied to the tendon versus a number of repetitions to reach a damage regime transition for the tendon. The method also includes generating one or more repetitive stress data sets that describe the tendon, and combining the S-N curves, or data derived therefrom, with the repetitive stress data sets to predict damage to the tendon under one or more conditions to produce a tendon damage model. In addition, the method also includes generating at least one guideline for tendon material repetitive stress for the tendon from the tendon damage model, wherein the guideline comprises a posture of the tendon, a number of repetitions of a given movement of the tendon, a force applied to the tendon, a duration of maintaining a given posture of the tendon, a duration of a repetition of a given movement of the tendon, a duration of a given force applied to the tendon, and a combination thereof, thereby generating the tendon damage model, which is used to obtain at least one guideline.

The methods of the present disclosure include various aspects. In some aspects, for example, the methods include combining multiple S-N curves for the physical regimes to produce at least one combined S-N curve. In certain aspects, the methods include applying at least one cumulative damage model when combining the S-N curves, or the data derived therefrom, with the repetitive stress data sets to predict the damage to the tendon under the one or more conditions. In some aspects, the methods include obtaining the S-N curve data sets using one or more data sources comprising medical diagnostic techniques, such as ultrasound data, computerized axial tomography (CAT) scan data, magnetic resonance imaging (MRI) scan data, destructive testing data, cadaver material, animal material, polymer surrogate material, molecular dynamic modeling (MDM) data, publication data, and a combination thereof.

In certain aspects, the tendon comprises a supraspinatus tendon. In some aspects, the tendon comprises a teres minor tendon, an infraspinatus tendon, a supraspinatus tendon, a subscapularis tendon, a deltoid tendons, a biceps tendon, a triceps tendon, a brachioradialis tendon, a supinator tendon, a flexor carpi radialis tendon, a flexor carpi ulnaris tendon, an extensor carpi radialis tendon, an extensor carpi radialis brevis tendon, an iliopsoas tendon, an obturator internus tendon, an adductor longus tendon, an adductor brevis tendon, an adductor magnus tendon, a gluteus maximus tendon, a gluteus medius tendon, a quadriceps tendon, a patellar tendon, a hamstring tendon, a sartorius tendon, a gastrocnemius tendon, an Achilles tendon, a soleus tendon, a tibialis anterior tendon, a peroneus longus tendon, a flexor digitorum longus tendon, an interosseus tendon, a flexor digitorum profundus tendon, an abductor digiti minimi tendon, an opponens pollicis tendon, a flexor pollicis longus tendon, an extensor tendon, an abductor pollicis tendon, a flexor hallucis longus tendon, a flexor digitorum brevis tendon, a lumbrical tendon, an abductor hallucis tendon, a flexor digitorum longus tendon, an abductor digiti minimi tendon, an ocular tendon, a levator palpebrae tendon, a masseter tendon, a temporalis tendon, a trapezius tendon, a sternocleidomastoid tendon, a semispinalis capitis tendon, a splenius capitis tendon, a mylohyoid tendon, a thyrohyoid tendon, a sternohyoid tendon, a rectus abdominis tendon, an external oblique tendon, a transversus abdominis tendon, a latissimus dorsi tendon, an erector spinae tendon, and a combination thereof. In some aspects, the tendon comprises a mammalian tendon. In certain of these aspects, the mammalian tendon comprises a human tendon. In other aspects, the tendon comprises a non-mammalian tendon.

In certain aspects, the methods include combining the S-N curves, or data derived therefrom, and the repetitive stress data sets with healing data to predict damage to the tendon under one or more conditions. In some aspects, the present disclosure provides a method of predicting tendon damage in a subject that includes obtaining one or more usage data sets for at least one tendon in the subject, and comparing the usage data sets to the guideline for tendon material repetitive stress generated by the method, thereby predicting the tendon damage in the subject. In certain aspects, the physical regimes comprise a no damage regime, a sub-rupture damage regime, a crack initiation regime, a fracture regime or curve, and a combination thereof. In some aspects, one or more of the steps are at least partially computer implemented.

In some aspects, the methods include generating at least one guideline for tendon material repetitive stress for the tendon from the tendon damage model, wherein the guideline comprises a posture and/or position of the tendon, a number of repetitions of a given movement of the tendon, a force applied to the tendon, a duration of maintaining a given posture of the tendon, a duration of a repetition of a given movement of the tendon, a duration of a given force applied to the tendon, and a combination thereof. In some of these aspects, the guideline for tendon material repetitive stress comprises one or more recommended use/rest cycles for the tendon under one or more sets of usage conditions. In certain of these aspects, the methods include validating the guideline for tendon material repetitive stress. In some of these aspects, the methods include individualizing the guideline for a given subject by applying one or more demographic variables for the subject to the guideline. In certain of these aspects, the methods include using task information when generating the guideline. In certain of these aspects, the task information comprises a tool weight and/or a force vector.

In certain aspects, the methods include estimating at least one stress distribution in the tendon to generate the repetitive stress data sets. In some of these aspects, the methods include estimating the stress distribution in the tendon using at least one dimension of the tendon. In certain of these aspects, the dimension comprises at least one cross-sectional area of the tendon. In some of these aspects, the methods include estimating the stress distribution in the tendon using at least one cycle curve that comprises a plot of at least one force applied to the tendon versus the number of repetitions to failure of the tendon. In certain of these aspects, the force is determined at one or more postures of the tendon. In some of these aspects, the methods include determining the force using estimating and/or modeling techniques, such as finite element modeling (FEM) and/or electromyography (EMG). In some of these aspects, the methods include using task information when determining the force applied at the postures of the tendon. In some aspects, the task information comprises a tool weight and/or a force vector.

In other aspects, the present disclosure provides a system, comprising a controller comprising, or capable of accessing, computer readable media comprising non-transitory computer-executable instructions which, when executed by at least one electronic processor perform at least: generating one or more S-N curves for one or more physical regimes of at least one tendon from one or more S-N curve data sets, wherein a given S-N curve comprises a plot of a magnitude of stress applied to the tendon versus a number of repetitions to failure of the tendon, and combining the S-N curves, or data derived therefrom, with one or more repetitive stress data sets to generate a tendon damage model.

In another aspect, the present disclosure provides a computer readable media comprising non-transitory computer-executable instructions which, when executed by at least one electronic processor perform at least: generating one or more S-N curves for one or more physical regimes of at least one tendon from one or more S-N curve data sets, wherein a given S-N curve comprises a plot of a magnitude of stress applied to the tendon versus a number of repetitions to failure of the tendon, and combining the S-N curves, or data derived therefrom, with one or more repetitive stress data sets to generate a tendon damage model.

In some aspects, the instructions of the systems or computer readable media disclosed herein further perform at least: combining multiple S-N curves for the physical regimes to produce at least one combined S-N curve. In certain aspects, the instructions of the systems or computer readable media disclosed herein further perform at least: applying at least one cumulative damage model when combining the S-N curves, or the data derived therefrom, with the repetitive stress data sets to predict the damage to the tendon under the one or more conditions. In some aspects, the instructions of the systems or computer readable media disclosed herein further perform at least: obtaining the S-N curve data sets using one or more data sources comprising medical diagnostic techniques, such as ultrasound data, computerized axial tomography (CAT) scan data, magnetic resonance imaging (MRI) scan data, destructive testing data, cadaver material, animal material, polymer surrogate material, molecular dynamic modeling (MDM) data, publication data, and a combination thereof. In some aspects, the instructions of the systems or computer readable media disclosed herein further perform at least: combining the S-N curves, or data derived therefrom, and the repetitive stress data sets with healing data to predict damage to the tendon under one or more conditions. In certain aspects, the instructions of the systems or computer readable media disclosed herein further perform at least: obtaining one or more usage data sets for at least one tendon in the subject, and comparing the usage data sets to the guideline for tendon material repetitive stress to predict tendon damage in a subject.

In some aspects, the instructions of the systems or computer readable media disclosed herein further perform at least: generating at least one guideline for tendon material repetitive stress for the tendon from the tendon damage model, wherein the guideline comprises a posture of the tendon, a number of repetitions of a given movement of the tendon, a force applied to the tendon, a duration of maintaining a given posture of the tendon, a duration of a repetition of a given movement of the tendon, a duration of a given force applied to the tendon, and a combination thereof. In certain aspects, the instructions of the systems or computer readable media disclosed herein further perform at least: validating the guideline for tendon material repetitive stress. In some of these aspects, the instructions of the systems or computer readable media disclosed herein further perform at least: individualizing the guideline for a given subject by applying one or more demographic variables for the subject to the guideline. In some of these aspects, the instructions of the systems or computer readable media disclosed herein further perform at least: using task information when generating the guideline. In certain of these aspects, the instructions of the systems or computer readable media disclosed herein further perform at least: estimating at least one stress distribution in the tendon to generate the repetitive stress data sets. In some of these aspects, the instructions of the systems or computer readable media disclosed herein further perform at least: estimating the stress distribution in the tendon using at least one dimension of the tendon. In some of these aspects, the instructions of the systems or computer readable media disclosed herein further perform at least: estimating the stress distribution in the tendon using at least one cycle curve comprises a plot of at least one force applied to the tendon versus the number of repetitions to failure of the tendon.

DRAWINGS

The above and/or other aspects and advantages will become more apparent and more readily appreciated from the following detailed description of examples, taken in conjunction with the accompanying drawings, in which:

FIG. 1 is a flow chart that schematically depicts exemplary method steps according to some aspects disclosed herein;

DETAILED DESCRIPTION

Figure 2:
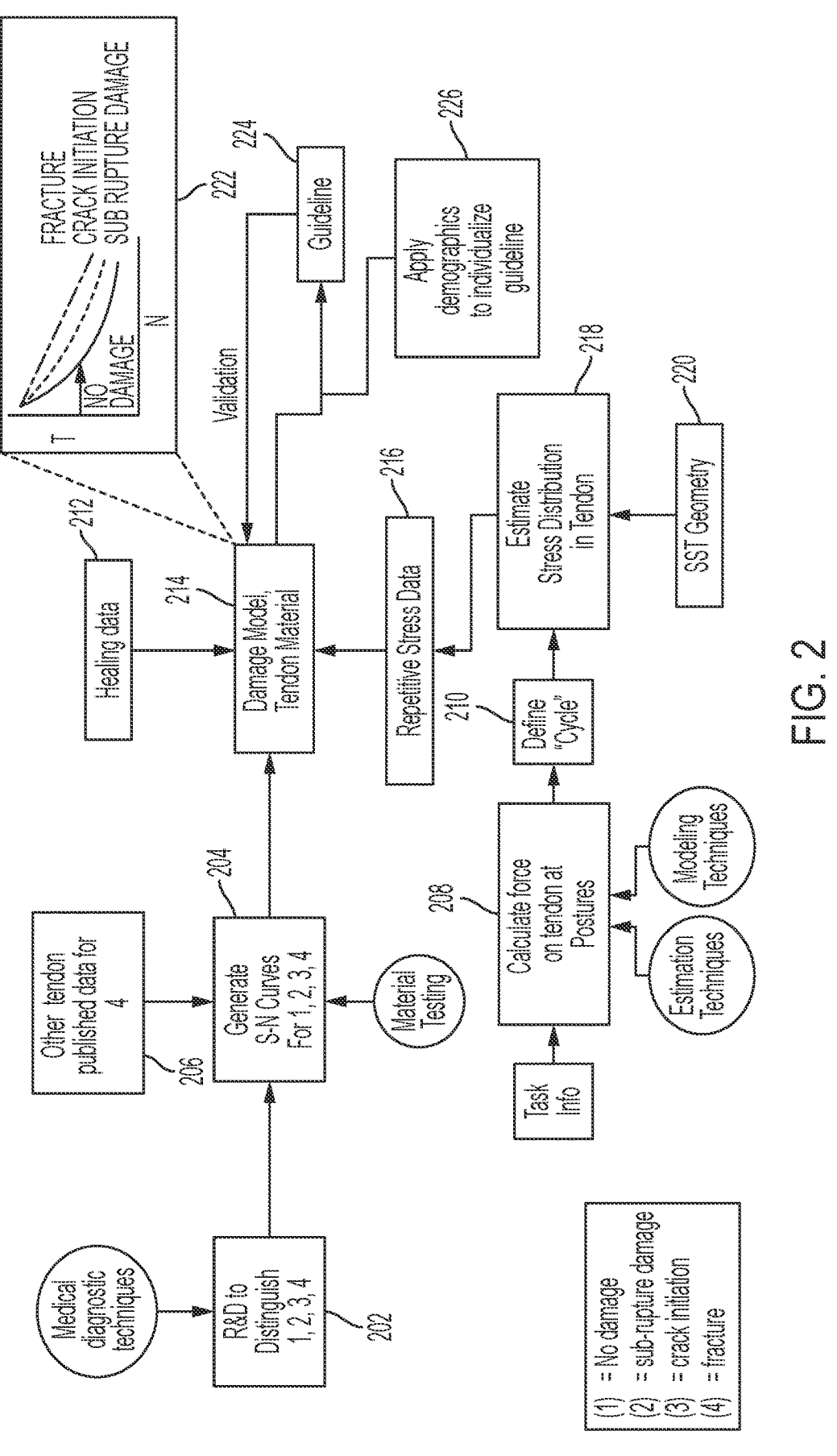
FIG. 2 is a schematic diagram that depicts exemplary method steps according to some aspects disclosed herein.

Exemplary aspects will now be described more fully with reference to the accompanying drawings. Examples of the disclosure, however, can be embodied in many different forms and should not be construed as being limited to the examples set forth herein. Rather, these examples are provided so that this disclosure will be thorough and complete, and will fully convey the scope to those skilled in the art. In the drawings, some details may be simplified and/or may be drawn to facilitate understanding rather than to maintain strict structural accuracy, detail, and/or scale.

It will be understood that when an element is referred to as being "on," "associated with," "connected to," "electrically connected to," or "coupled to" to another component, it may be directly on, associated with, connected to, electrically connected to, or coupled to the other component or intervening components may be present. In contrast, when a component is referred to as being "directly on," "directly associated with," "directly connected to," "directly electrically connected to," or "directly coupled to" another component, there are no intervening components present. As used herein, the term "and/or" includes any and all combinations of one or more of the associated listed items.

It will be understood that although the terms first, second, etc., may be used herein to describe various elements, components, and/or directions, these elements, components, and/or directions should not be limited by these terms. These terms are only used to distinguish one element, component, and/or direction from another element, component, and/or direction. For example, a first element, component, or direction could be termed a second element, component, or direction without departing from the teachings of examples.

Spatially relative terms, such as "beneath," "below," "lower," "above," "upper," and the like may be used herein for ease of description to describe the relationship of one component and/or feature to another component and/or feature, or other component(s) and/or feature(s), as illustrated in the drawings. It will be understood that the spatially relative terms are intended to encompass different orientations of the device in use or operation in addition to the orientation(s) depicted in the figures.

As used herein, a given "component" and corresponding "component connector" refers to at least two components that are structured or otherwise operable to be joined, operably connected, or otherwise associated with one another. In certain aspects, one component is structured or otherwise operable to be joined, operably connected, or otherwise associated with multiple component connectors. In some aspects, one component connector is structured or otherwise operable to be joined, operably connected, or otherwise associated with multiple components.

As used herein, "subject" refers to an animal, such as a mammalian species (e.g., human) or avian (e.g., bird) species or to non-mammalian species (e.g., fish, mollusks, reptiles, amphibians, etc). More specifically, a subject can be a vertebrate, e.g., a mammal such as a mouse, a primate, a simian or a human. Animals include farm animals (e.g., production cattle, dairy cattle, poultry, horses, pigs, and the like), sport animals, and companion animals (e.g., pets or support animals). A subject can be a healthy individual, an individual that has or is suspected of having a disease or a predisposition to the disease, or an individual that is in need of therapy or suspected of needing therapy.

The terminology used herein is for the purpose of describing particular examples only and is not intended to be limiting of examples. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which examples belong. It will be further understood that terms, such as those defined in commonly used dictionaries, should be interpreted as having a meaning that is consistent with their meaning in the context of the relevant art and should not be interpreted in an idealized or overly formal sense unless expressly so defined herein.

I. Introduction

The present disclosure relates to methods, systems, computer readable media and related models for determining and predicting tendon use based, in certain aspects, on materials sciences principles such as force (e.g., at different postures), stress distribution, stress data, and material (e.g., tendon) performance parameters (e.g., healthy state, healing, accumulating damage, and damaged). The present disclosure identifies useful correlations between materials science principles and tendons. In some applications, the predictive model is used in addressing ergonomic issues related to a task to inform and establish guidelines to prevent or otherwise mitigate potential for an injury. Although much of the present disclosure focuses on shoulder injuries and the supraspinatus tendon, the methods and related aspects disclosed herein can also be applied to essentially any soft tissue, such as intervertebral (spinal) discs, ligaments, tendons, and tendon system of interest and in biomimicry applications, such as in the design of artificial tendons.

By way of further introduction, using the shoulder for performing work in a workplace is a challenge in extreme work environments. Shoulder injuries also often occur outside of the workplace, e.g., while at home and while participating in sports or other human activities. Current guidelines do not provide clear, acceptable limits for shoulder-based work activity in a workplace and they do not account for the interaction of posture, force and repetition, nor the interaction of posture, force, repetition, duration, and vibration. Practitioners who are not able to simply eliminate shoulder movements are faced with degrees of unknown risk. Therefore, robust threshold limit guidelines for shoulder-joint demand are needed that address the complex nature of upper extremity work that includes the interaction of force, repetition and posture and work/rest cycles. Such guidelines are very helpful to industrial engineers and ergonomists, but can also be helpful for physicians, physical therapists, sports medicine practitioners, and sports coaches, among others.

i. Occupational and Non-Occupational Shoulder Disorders are Significant

It has been well documented that shoulder disorders are common and frequent in extreme workplaces such as heavy manufacturing, welding, fisheries, meat processing, heavy machining, auto repair and painting. U.S. Bureau of Labor Statistics 2013 data show that cumulative trauma injuries to the shoulder accounted for 15% of all workplace musculoskeletal injuries, exceeded only by lower back and general back injuries; however, shoulder injuries tended to be more severe, resulting in more time loss. The typical shoulder injury resulted in 21 lost work days, almost double other musculoskeletal injuries at 11 days and triple for back injuries at seven days of lost work. Each day lost by an employee has a profound effect not only on the employee and their family, but also production schedules, product quality, and co-workers who perform additional work when a team member is absent and injured.

ii. Shoulder Function

Shoulder mechanisms permit the placement, functioning, and control of the hand, the most useful part of the human body for manual labor or tool-intensive assembly. Hands, and therefore arms and shoulders, move to weld, paint, drill, cut, gut fish, or handle materials. The tool, hand, and shoulder system are often positioned overhead or in hard to reach places. The shoulder complex must support the weight of the arm, any tools being held to perform work, and force applied. Most manual work involving tools include tasks to be repeated many times during the course of a work period.

A neutral shoulder posture is the upper arm straight and hanging alongside the body. Every time a shoulder is out of its neutral position, tendons are placed under tensile force, creating stress within the tendon. Each time the shoulder moves away from neutral position, force and repetition occur, exposing the tendon to cumulative fatigue damage.

iii. Risk Guidelines are Insufficient

Studies linking shoulder pain or rotator cuff injuries to workplace factors identify overhead work (defined as elbows above shoulders), applied force, repetitive motion, and physical loads as significant contributors. However, the quality of these studies varies, and evidence did not consistently demonstrate a significant dose-response relationship although since then, two studies have related upper arms elevated above 90° with specific outcomes of tendon damage detected in MRI or impingement surgery. A review specifically focused on evidence of workplace factors in rotator cuff tendon disorder outcomes and found research lacking.

Even for studies with a specific outcome, the exposure assessments in these research papers were too gross, and classification of outcome still not specific enough to estab-lish a strong quantitative association between 'dose and response' or 'exposure and risk'. As a result, current published guidelines for shoulder-demand injury risk are insufficient for use in occupational ergonomics injury prevention programs. These guidelines simply recommend reduction or elimination of overhead or extended shoulder postures; they do not specify to what degree reduction is needed to significantly impact injury rates.

While eliminating repetitive, awkward or taxing shoulder use is infeasible in some industries, it could be ameliorated. Without available risk thresholds, the question persists as to what degree these risk factors should be reduced to prevent injury. The question is further complicated because this type of work can involve many repetitive motions (painting) and/or forces (drilling) and/or loads (welding). Any useful guideline should also include risk factor interaction and work/rest cycles.

iv. A New Approach

Given the inability of establishing causality with epidemiological data alone, an alternative approach is needed. The models and related aspects disclosed herein bridge many of the gaps that traditional epidemiological studies have not been able to close and instead uses a fatigue model of cumulative damage to predict and prevent injuries in certain aspects.

The term "fatigue" is used throughout this disclosure in its mechanical sense—structural degradation from repeated forces—rather than physiological fatigue, which is the inability to perform activity because muscle contractile forces are reduced. The term "resultant force" is used to indicate the tensile force on the tendon caused by the tool weight, body segment posture, and force applied to the tool by the worker. More generally, "resultant force" refers to a combination of the forces acting on soft tissue during work, including posture (e.g., shoulder position), vibration, tool weight, force vector applied at the hand, arm weight, etc. Tensile force is relevant to shoulders, but other soft tissue, such as intervertebral discs, can experience compressive force. Other types of soft tissue can experience both compressive and tensile forces.

v. Tendon Subrupture

When people are engaged in physical activity, the effects of repeated stress on soft tissues result in small fissures often referred to as microtrauma or subruptures. Subruptures themselves are not harmful to the body because the body will repair itself to become stronger given a sufficient recovery period; this is the underlying benefit of exercise. With insufficient recovery period, the tendon becomes damaged and eventually an injury will occur. Sufficient recovery period for tendon use (or overuse) was previously undetermined, unknown, or undefined.

Robust guidelines are needed that provide clear, acceptable limits and rest cycles for shoulder-based work activity, which account for the interactions between posture, force, duration, vibration, and repetition.

The models for supraspinatus tendon fatigue and repair periods disclosed herein are advantageous for heavy industry, especially where overhead work, repetition, and force exist, and for sports. Tendons behave like materials, with predictable fatigue failure at given stress levels and cycles, but they are also able to self-repair.

The approaches presented herein draw, for example, on principles from materials science and medicine to propose such models. The models can be used to set exposure limits and create usable work/rest cycles to predict and prevent shoulder overuse injuries, leading to a significant change in current approaches to mitigating and reducing shoulder injuries.

In certain aspects, the models disclosed herein do not include all aspects of tendon behavior. The prevalence of occupational shoulder injuries outweighs the limited amount of research currently taking place and much opportunity exists for collaborative research between such diverse groups as aerospace engineers, fatigue experts, orthopedic surgeons, and industrial ergonomists, with potentially immense benefits for worker health.

The models disclosed herein can be used to, for example, redesign work practices exceeding reasonable tendon strain or stress thresholds, create work-rest cycles based on collagen damage and repair rates, identify individuals for whom the model is not conservative, and implement strength training to improve tendon material properties.

Note that the disclosed techniques are not limited to tendons. As set forth herein, an example is presented by way of illustration rather than limitation in reference to shoulder tendons. However, examples are not so limited. Other types of soft tissue, such as intervertebral (spinal) discs and ligaments are amenable to analysis and injury amelioration using examples disclosed herein.

II. Exemplary Methods

Figure 3:
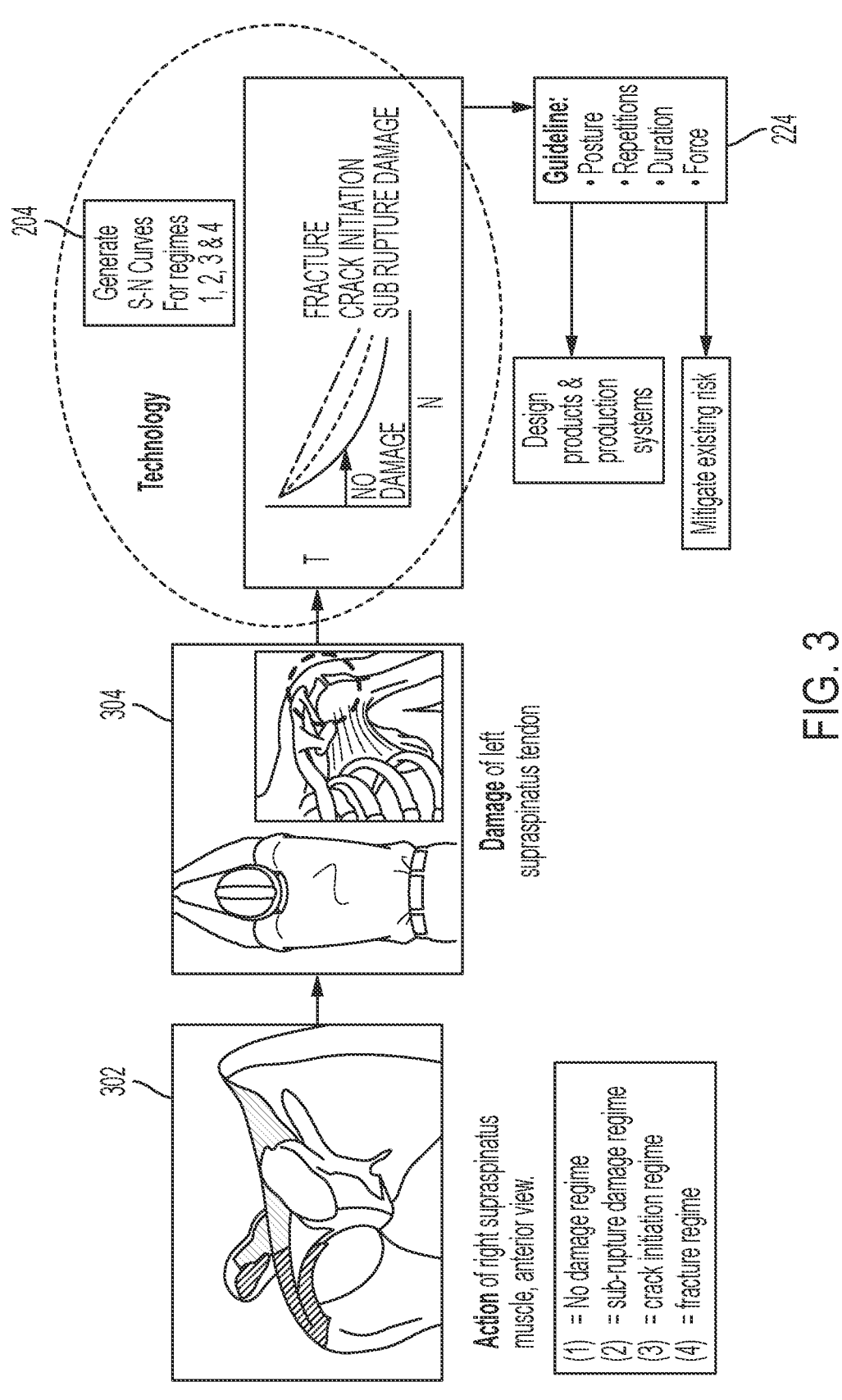
FIG. 3 is a schematic diagram that depicts exemplary method steps according to some aspects disclosed herein.

The present disclosure provides assorted methods of generating a tendon damage model and of generating guidelines for tendon material repetitive stress. Certain aspects of these methods are schematically shown in FIGS. 1-3. As shown, method 100 includes generating one or more S-N curves for one or more physical regimes of at least one tendon from one or more S-N curve data sets (step 102, 204). A given S-N curve typically comprises a plot of a magnitude of stress applied to the tendon versus a number of repetitions to failure of the tendon. Model components for each of the above processes will identify four (4) regimes of damage accumulation: 1) no damage; 2) micro-damage (subrupture) accumulation; 3) damage accumulation in the form of a growing tear or fissure, cellular matrix damage or other biological damage; and 4) a state of catastrophic failure or separation of the tendon structure. Method 100 also includes generating one or more repetitive stress data sets that describe the tendon (step 104, 216). Method 100 also includes combining the S-N curves (222), or data derived therefrom, with the repetitive stress data sets (216) to predict damage to the tendon under one or more conditions to generate a tendon damage model (step 106, 216) (e.g., physical or tangible representations or information of the tendon damage under a given set of conditions). In certain aspects, method 100 also typically includes generating at least one guideline for tendon material repetitive stress for the tendon from the tendon damage model (step 108, 224). As used herein, the term "guideline" refers to a recommended set of evidence-based maximum acceptable limits, in terms of force (e.g., vibration, tool weight, force vector applied at the hand, arm weight, etc.), posture, position, frequency, duration and/or recovery, intended to safeguard human tissue material from the risk of injury due to tendon damage during human activity such an manufacturing or other processes. In some aspects, the guideline comprises a posture of the tendon, a number of repetitions of a given movement of the tendon, a force applied to the tendon, a duration of maintaining a given posture of the tendon, a duration of a repetition of a given movement of the tendon, a duration of a given force applied to the tendon, and a combination thereof. As also shown, the methods also include evaluating the action of a given muscle (302) and damage of a given tendon (304) in certain aspects.

The methods of the present disclosure include various aspects. In some aspects, for example, the methods include combining multiple S-N curves for the physical regimes to produce a combined S-N curve (222). In certain aspects, the methods include applying a cumulative damage model when combining the S-N curves (204), or the data derived therefrom, with the repetitive stress data sets (216) to predict the damage to the tendon under one or more conditions. In some aspects, the methods include obtaining the S-N curve data sets using one or more data sources comprising medical diagnostic techniques, such as ultrasound data, computerized axial tomography (CAT) scan data, magnetic resonance imaging (MRI) scan data, destructive testing data, cadaver material, animal material, polymer surrogate material, molecular dynamic modeling (MDM) data, publication data, and a combination thereof (202, 204, 206).

Essentially any tendon can be evaluated as part of the methods disclosed herein. Some exemplary tendons that are optionally used, include a teres minor tendon, an infraspinatus tendon, a supraspinatus tendon, a subscapularis tendon, a deltoid tendons, a biceps tendon, a triceps tendon, a brachioradialis tendon, a supinator tendon, a flexor carpi radialis tendon, a flexor carpi ulnaris tendon, an extensor carpi radialis tendon, an extensor carpi radialis brevis tendon, an iliopsoas tendon, an obturator internus tendon, an adductor longus tendon, an adductor brevis tendon, an adductor magnus tendon, a gluteus maximus tendon, a gluteus medius tendon, a quadriceps tendon, a patellar tendon, a hamstring tendon, a sartorius tendon, a gastrocnemius tendon, an Achilles tendon, a soleus tendon, a tibialis anterior tendon, a peroneus longus tendon, a flexor digitorum longus tendon, an interosseus tendon, a flexor digitorum profundus tendon, an abductor digiti minimi tendon, an opponens pollicis tendon, a flexor pollicis longus tendon, an extensor tendon, an abductor pollicis tendon, a flexor hallucis longus tendon, a flexor digitorum brevis tendon, a lumbrical tendon, an abductor hallucis tendon, a flexor digitorum longus tendon, an abductor digiti minimi tendon, an ocular tendon, a levator palpebrae tendon, a masseter tendon, a temporalis tendon, a trapezius tendon, a sternocleidomastoid tendon, a semispinalis capitis tendon, a splenius capitis tendon, a mylohyoid tendon, a thyrohyoid tendon, a sternohyoid tendon, a rectus abdominis tendon, an external oblique tendon, a transversus abdominis tendon, a latissimus dorsi tendon, an erector spinae tendon, and a combination thereof. In some aspects, the tendon comprises a mammalian tendon. In certain of these aspects, the mammalian tendon comprises a human tendon.

In certain aspects, the methods include combining the S-N curves, or data derived therefrom, and the repetitive stress data sets with healing data to predict damage to the tendon under one or more conditions (212). In some aspects, the present disclosure provides a method of predicting tendon damage in a subject that includes obtaining one or more usage data sets for at least one tendon in the subject, and comparing the usage data sets to the guideline for tendon material repetitive stress generated by the method, thereby predicting the tendon damage in the subject. In certain aspects, the physical regimes comprise a no damage regime, a sub-rupture damage regime, a crack initiation regime, a fracture regime or curve, and a combination thereof. In some aspects, one or more of the steps are at least partially computer implemented. Systems and related computer readable media are described further herein.

In some aspects, the methods include generating at least one guideline (224) for tendon material repetitive stress for the tendon from the tendon damage model (214) in which the guideline comprises a posture of the tendon, a number of repetitions of a given movement of the tendon, a force applied to the tendon, a duration of maintaining a given posture of the tendon, a duration of a repetition of a given movement of the tendon, a duration of a given force applied to the tendon, and a combination thereof. In some of these aspects, the guideline for tendon material repetitive stress comprises one or more recommended use/rest cycles for the tendon under one or more sets of usage conditions. Typically, the methods include validating the guideline for tendon material repetitive stress. In some of these aspects, the methods include individualizing the guideline for a given subject by applying one or more demographic variables for the subject to the guideline (226). In certain of these aspects, the methods include using task information when generating the guideline (228). In certain of these aspects, the task information comprises a tool weight and/or a force vector.

In certain aspects, the methods include estimating at least one stress distribution in the tendon to generate the repetitive stress data sets (218). In some of these aspects, the methods include estimating the stress distribution in the tendon using at least one dimension of the tendon (220). In certain of these aspects, the dimension comprises at least one cross-sectional area of the tendon. In some of these aspects, the methods include estimating the stress distribution in the tendon using at least one cycle curve that comprises a plot of at least one force applied to the tendon versus the number of repetitions to failure of the tendon (210). In certain of these aspects, the force is determined at one or more postures of the tendon (208). In some of these aspects, the methods include determining the force using an estimation and/or modeling technique, such as finite element modeling (FEM) and/or electromyography (EMG). In some of these aspects, the methods include using task information when determining the force applied at the postures of the tendon. In some aspects, the task information comprises a tool weight and/or a force vector.

In some aspects, the process of combining S-N curves involves cumulative damage modeling around multiple curves and healing. To illustrate, an example might include a repetitive stress data set (this set might correspond to the exposure that a subject might accrue during the course of one task, for example) that comprises:

Task A Force: 150N Repetitions: 50
Task B Force: 100N Repetitions: 500
Task C Force: 50N Repetitions: 5000

The Repetition numbers are derived from observing or sampling the task in certain aspects. The Stress numbers are derived by the digital model of a subject's hand/arm position while performing the task, plus any load the subject is carrying in some aspects. The output would be force (N). Stress is force divided by cross sectional area of the tendon (e.g., an SST Geometry model), which is 50 mm$^2$ in this example. This creates Task A Stress=3 MPa, Task B Stress=2 MPa, and Task C Stress=1 MPa. In this illustration, some information is also available about the S-N curve for where no damage occurs and that the no damage regime ends (and subrupture starts) at 1000 cycles at 4 MPa (this is one point along the curve).

All of these numbers are combined to ascertain the amount of damage to the tendon under consideration. In some aspects, Miner's Rule is used as part of this process. In Miner's rule, if 1 is exceeded, that means the S-N curve selected to compare is exceeded. In this case, since the no damage regime is selected, exceeding 1 means that the no damage regime no longer applies and instead, one of the other regimes does apply.

These tasks are combined with the no damage regime limit and (3 MPa*50+2 MPA*500+1 MPa*5000)/(4 MPa*1000)=1.53 is obtained. This means that the no damage regime is exceeded since it is >1. Also, if a given guideline specifies that no damage at all is desired, then the guideline has been exceeded. Thus, the next regime (e.g., subrupture) would need to be calculated to and maybe the next one after, if >1, and so on up to the Fracture regime. In some aspects, healing data is also applied if multiple tasks are combined with rest periods in between (e.g., a percentage reduction in exposures, moving to a lower point on the curve, etc.).

The calculations presented above in this illustration provide a point solution (just one number and one answer) for one iteration. For better model fidelity, this iteration could be run a number of times, sampling from distributions of, for example, SST geometries, the digital model for force on tendon, and optionally some variation in the repetitions. For example, this can be a model run multiple times with slightly different probabilistic inputs similar to a Monte Carlo simulation. This provides an output of the risk with some boundaries or bands around it (e.g., a 95% confidence interval, etc.). Optionally, other variables, such as demographics are also added to the model.

Figure 4:
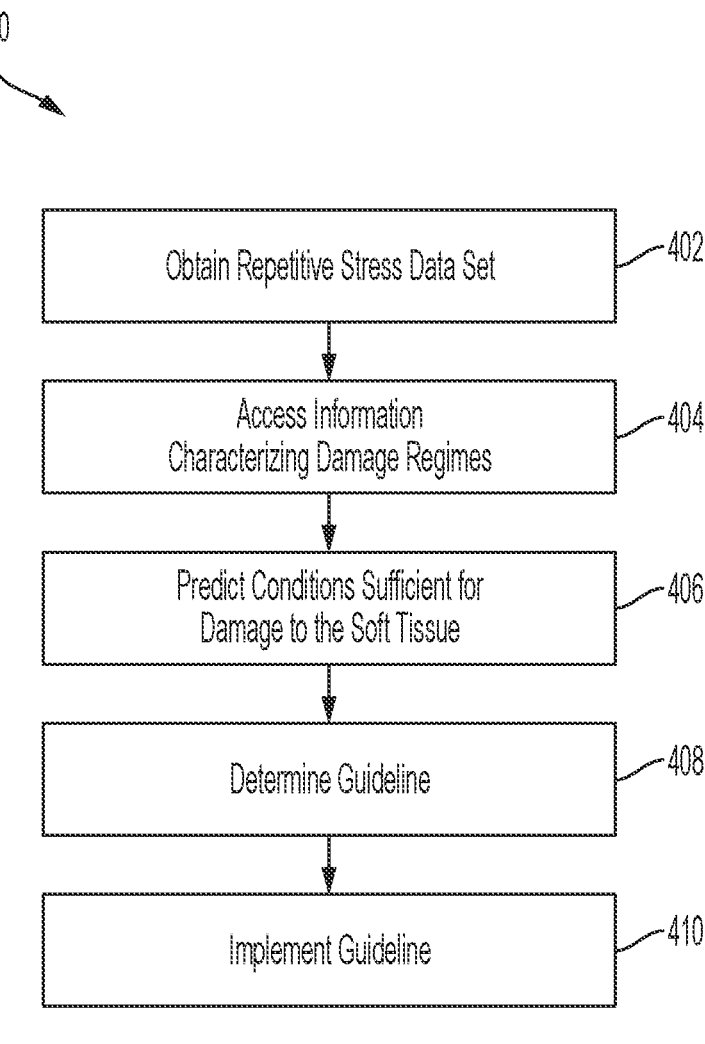
FIG. 4 is a flow chart depicting a method of providing at least one guideline for reducing a risk of a repetitive stress injury to a tendon according to various examples.

FIG. 4 is a flow chart depicting a method 400 of reducing (e.g., eliminating) repetitive stress injuries to soft tissue in performing a process according to various examples. Method 400 can utilize material science properties of such soft tissue to determine guidelines that, when implemented as described presently in reference to method 400, reduce the potential for injuries to those performing the process. Method 400 can be partially implemented using system 500, as shown and described below in reference to FIG. 5, for example. Method 400 further includes extra-computer actions that provide improvements in the field of industrial hygiene. Such actions include, for example, obtaining a repetitive stress data set related to the soft tissue and to the process (e.g., a description of force per area of the soft tissue and a number of repetitions) and implementing the guidelines to reduce the potential for repetitive stress injuries to an individual in a process.

Method 400 can be used to ameliorate repetitive stress injuries of workers performing a part of a manufacturing process, for example. Each worker can have one or more tasks that form part of the manufacturing process, e.g., on an assembly line. The tasks for each worker can be modified by the one or more guidelines produced by method 400. Alternately, method 400 can be used to ameliorate repetitive stress injuries of an athlete executing a training program, for example. The athlete can have one or more exercises that form part of the training program. The exercises can be modified by the one or more guidelines produced by method 400. In general, method 500 can be practiced to ameliorate repetitive stress injuries in any type of process that includes repetitive movements by a person, not limited to manufacturing or athletic processes.

Method 400 can be used to ameliorate injuries to any of a variety of soft tissues. According to some examples, method 400 can be used to ameliorate injuries to tendons or tendon complexes. Examples of such tendons and tendon complexes are presented above in reference to FIGS. 1-3. Alternately, method 400 can be used to ameliorate injuries to connective tissue or musculoskeletal soft tissue. In general, non-limiting examples of soft tissues for which examples can be implemented include tendons, tendon complexes, intervertebral (spinal) discs, and ligaments.

At 402, method 400 obtains at least one repetitive stress data set related to the soft tissue and to the process. The repetitive stress data sets can be in the form of computer files, e.g., in tab-delimited or comma-separated value (CSV) format. The repetitive stress data sets can be obtained by being read from persistent electronic storage by a computer, or by the data being entered into file format and stored in the computer, by way of non-limiting examples.

According to some examples, each repetitive stress data set can represent the exposure that a subject might accrue over the course of completing one task that forms part of the overall process. The exposure can be in the form of a number of repetitions and a force on the soft tissue per repetition. The force can be expressed in Newtons (N) for example. Alternately, each repetitive stress data set can be in the form of a number of repetitions and a stress on the soft tissue per repetitions. The stress can be resultant stress, including stress due to posture (e.g., shoulder position), vibration, tool weight, force vector applied at the hand, arm weight, etc. The stress can be expressed in Megapascals (MPa), for example.

Each repetitive stress data set can further include a description of a movement for each repetition, e.g., in narrative form. Multiple repetitive stress data sets can account for multiple types of movements. Method 400 can obtain the repetitive stress data set(s) by acquiring them in computer readable form (e.g., by user entry) and providing them to a computer program that performs the actions of, e.g., blocks 402, 404, 406, and at least part of 408.

At 404, method 400 accesses information characterizing at least two damage regimes. The information can be in the form of computer files, e.g., as pairs for values in tab-delimited or comma-separated value (CSV) format. The information can be accessed by being read from persistent electronic storage by a computer, or by the information being received and stored in the computer, by way of non-limiting examples.

According to various examples, method 400 can access first information characterizing a first damage regime and second information characterizing a second damage regime. According to various examples, method 400 can further access third information characterizing a third damage regime. Each information can quantify a number of repetitions at a given stress for the soft tissue to transition out of the respective damage regime. For example, the first information can quantify a number of repetitions per given stress for the soft tissue to transition out of the first damage regime; the second information can quantify a number of repetitions per given stress for the soft tissue to transition out of the second damage regime, and, for examples that include a third damage regime, the third information can quantify a number of repetitions per given stress for the soft tissue to transition out of the third damage regime.

Each information can be in the form of a curve quantifying a number of repetitions at a given stress for the soft tissue to transition out of the respective damage regime, e.g., with stress as an independent variable and repetitions as a dependent variable. For example, each information can be in the form of an S-N curve, as described herein, according to various examples. When stored in a computer, such information can be in the form of a set of ordered pairs (S, R), where S represents stress and R represents a number of repetitions to transition out of the respective regime.

According to various examples, the first damage regime can be a no damage regime, the second damage regime can be a sub-rupture damage regime, and, for examples that include it, the third damage regime can be a tear propagation regime. (Note that any combination of two or more damage regimes can be used according to various examples, not limited to those explicitly set forth presently.) The no damage regime can represent a situation in which micro-damage (e.g., sub-ruptures) occur in the soft tissue at substantially the same rate as they are healed. Transition out of the no damage regime can represent sub-rupture accumulation at a rate faster than the healing rate for the respective soft tissue. The sub-rupture regime can represent a situation where the micro-damage (e.g., sub-rupture damage) accumulates, but no macroscopic tear has yet formed. Transition out of the sub-rupture regime can represent that a macroscopic tear has formed. The tear propagation regime can represent a situation where a tear has formed and is propagating through the soft tissue. Transition out of the tear propagation regime can represent that the soft tissue has fully ruptured.

Note that examples that incorporate either or both of the no damage regime and the sub-rupture regime can predict damage to subject soft tissue prior to the subject realizing that damage has occurred. For example, soft tissue within these regimes can be damaged, but cause no pain or discomfort to the subject.

At 406, method 400 predicts, based on at least the information characterizing the damage regimes and the repetitive stress data set, conditions sufficient for damage to the soft tissue. The damage can be any of: the soft tissue accumulating micro-damage at a rate faster than the healing rate of the soft tissue (e.g., a transition out of the first regime), the soft tissue experiencing a macroscopic tear (e.g., a transition out of the second regime), or the soft tissue experiencing a full rupture (e.g., a transition out of the third regime).

The prediction can utilize material science properties of the soft tissue to determine such conditions. According to some examples, the prediction can be performed as follows. First, if not already in terms of stress, the force data in the repetitive stress data set can be converted to units of stress. For example, the repetitive stress data set can be in terms of force on the soft tissue per repetition. By dividing such force by the cross-sectional area of the soft tissue, the repetitive stress data set is converted into units of stress per repetition (and/or per repetition). The system can store soft tissue cross sectional area data to that end. The soft tissue cross sectional area data can include average cross-sectional areas for various soft tissue types, specific cross sectional areas per demographic combination (e.g., sex, age, gender), or a combination of such data. Second, the repetitive stress data set is compared to the information characterizing the damage regimes. For example, for a repetitive stress data set that represents R repetitions at a stress level of S, that stress level S can be considered an independent variable in the information representing the current damage regime of the soft tissue, and the corresponding dependent variable R' in terms of a number of repetitions for transition out of the damage regime can be identified. Third, the number of repetitions R' of the identified dependent variable is compared with the number R of repetitions set forth in the repetitive stress data set. If the former is greater than the latter, then the soft tissue is predicted to remain in its current damage regime, and therefore no additional damage is predicted. If, however, the former is less than or equal to the latter, then the soft tissue is predicted to transition out of the respective damage regime. In that case, the soft tissue is predicted to undergo damage. Thus, the soft tissue is predicted to undergo damage when the number of repetitions R set forth in the repetitive stress data set for stress level S meets or exceeds the number of repetitions R' corresponding to S per the information characterizing the current damage regime for transition out of the current damage regime.

This process can be extended to include multiple repetitive stress data set. For example, the products of the repetitions and stress levels from the various repetitive set data sets can be summed. This sum can be compared to the product of a stress level and number of repetitions from the information characterizing the current damage regime. If the sum is greater, then the soft tissue is predicted to undergo damage. Otherwise, the soft tissue is predicted to remain in the current damage regime. Note that Miner's Rule, as described in the example above in reference to FIGS. 1-3, can be employed for this comparison.

At 408, method 400 determines, based on at least the predicting, at least one guideline for reducing a risk of a soft tissue material repetitive stress injury. In general, the guideline can reduce a number of repetitions and/or an amount of stress corresponding to actions in one or more of the repetitive stress data sets. Such parameters can be reduced until the calculations described above in reference to block 406 predict no damage. The parameters so reduced can form all or part of a guideline.

In general, the guideline can reduce the stress on the soft tissue by reducing the force on the soft tissue in any of a number of ways. The force on the soft tissue can be a resultant force on the soft tissue, the force being the result of posture (or position), weight (e.g., of the arm and/or holding an object such as a tool), applied force vector (e.g., pushing at the hand), vibration (from holding a vibrating object such as a hand tool), etc. According to some examples, the force is reduced by placing a limitation on any of the above parameters.

The force on the soft tissue can alternately, or in addition, be reduced placing a limitation on the position and/or posture of the subject's body or portion thereof, thus affecting a position and/or posture of the soft tissue. According to various examples, the guideline can include a limitation on at least one of a position of the soft tissue, and/or a posture of the soft tissue.

Here, "position" can refer to quantitative characterization of the subject's body or part thereof. For example, a position can be defined using measurement equipment, with units like length, angle, or x-y-z coordinates. For example, a tendon position can be defined at coordinates (0 cm, 5 cm, 1 cm), where origin (0 cm, 0 cm, 0 cm) is where the tendon attaches to the humerus, and the coordinates correspond to positions in the following planes as follows: x=saggital, y=transverse, and z=coronal. A position of a subject (or a portion of the subject's body) can be determined by attaching a motion tracking system to the subject according to various examples.

"Posture" can refer to qualitative characterizations of the subject's body or part thereof. A posture can be defined in terms of relative positions of identified landmarks. For example, a particular posture referred to as "overhead work" can be defined as the situation when the subject's elbow is above the subject's shoulder. In general, a posture can define a body position in a qualitative way, such that it can be observed and compared to another observation or position. A position of a subject (or a portion of the subject's body) can be determined by observational study by an ergonomist or industrial engineer according to various examples.

Alternately, or in addition, the force on the soft tissue can be reduced placing a limitation on a temporal duration of a movement, position, or posture. That is, the guideline can place a limitation on any, or a combination, of: a duration of maintaining a given posture of the soft tissue, a duration of maintaining a given position of the soft tissue, a duration of a repetition of a given movement of the soft tissue, and/or a duration of a given force applied to the soft tissue.

According to some examples, the guidelines can include imposed rest periods. Such examples can utilize a representation of the healing processes that counteract micro-damage or macro-damage. The rest periods can represent sufficient time for such healing processes to counteract any accumulated damage.

The guidelines can be output in any of a variety of forms. According to some examples, the guidelines are output in narrative form using pre-generated narrative templates. For example, if the computations indicate that the number of repetitions should be reduced from 1000 to 725, the guideline can populate these numbers into a template that reads in part, "The number of repetitions for action X should be reduced from Y to Z," where X, is replaced with a description of the action, Y is replaced by 1000, and Z is replaced by 725. The formatted guidelines can be output by displaying on a computer monitor, by email, or by any other techniques that provide the information to a person or process.

At 410, method 400 implements the guideline(s) in the process. To do so, method 400 can include providing the guidelines to workers on an assembly line, for examples in which the process is a manufacturing process. The workers can then alter their tasks accordingly. For examples in which the process is an athletic training process, the guidelines can be provided to the trainer, who alters the athlete's training plan accordingly. Further, the guidelines can be used to design production systems, products, work tasks, training plans, etc.

III. Exemplary Systems and Computer Readable Media

Figure 5:
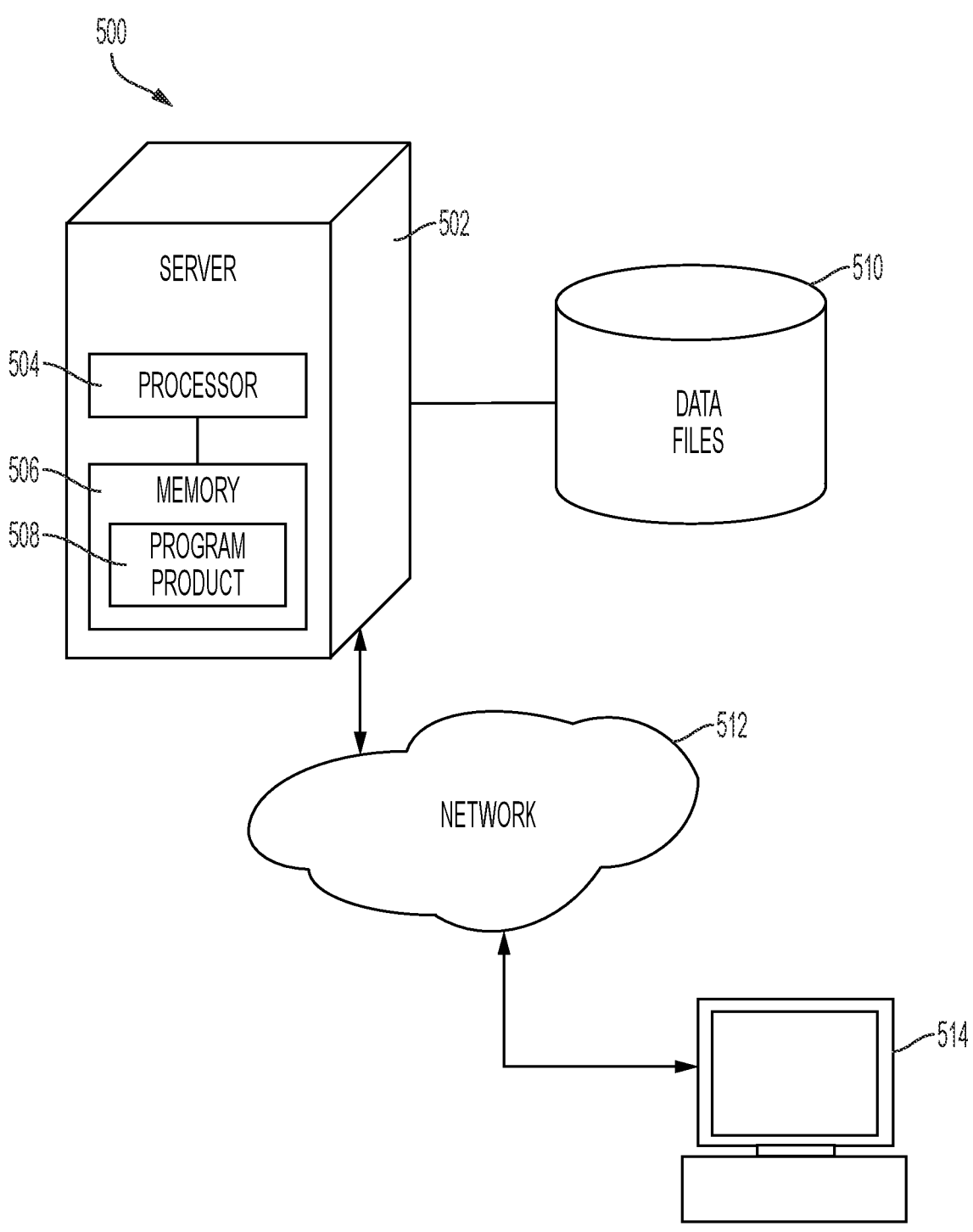
FIG. 5 is a schematic diagram of an exemplary system suitable for use with certain aspects disclosed herein.

The present disclosure also provides various systems and computer program products or machine readable media. In some aspects, for example, the methods described herein are optionally performed or facilitated at least in part using systems, distributed computing hardware and applications (e.g., cloud computing services), electronic communication networks, communication interfaces, computer program products, machine readable media, electronic storage media, software (e.g., machine-executable code or logic instructions) and/or the like. To illustrate, FIG. 5 provides a schematic diagram of an exemplary system suitable for use with implementing at least aspects of the methods disclosed in this application. As shown, system 500 includes at least one controller or computer, e.g., server 502 (e.g., a search engine server), which includes processor 504 and memory, storage device, or memory 506, and one or more other communication devices 514 (e.g., client-side computer terminals, telephones, tablets, laptops, other mobile devices, etc.) positioned remote from and in communication with the server 502, through electronic communication network 512, such as the Internet or other internetwork. Communication device 514 typically includes an electronic display (e.g., an internet enabled computer or the like) in communication with, e.g., server 502 computer over network 512 in which the electronic display comprises a user interface (e.g., a graphical user interface (GUI), a web-based user interface, and/or the like) for displaying results upon implementing the methods described herein. In certain aspects, communication networks also encompass the physical transfer of data from one location to another, for example, using a hard drive, thumb drive, or other data storage mechanism. System 500 also includes program product 508 stored on a computer or machine readable medium, such as, for example, one or more of various types of memory, such as memory 506 of server 502, that is readable by the server 502, to facilitate, for example, an executable by one or more other communication devices, such as computer 514 (schematically shown as a desktop or personal computer). In some aspects, system 500 optionally also includes at least one database server, such as, for example, server 510 associated with an online website having data stored thereon (e.g., control sample or comparator result data, indexed customized therapies, etc.) searchable either directly or through server 502. System 500 optionally also includes one or more other servers positioned remotely from server 502, each of which are optionally associated with one or more database servers 510 located remotely or located local to each of the other servers. The other servers can beneficially provide service to geographically remote users and enhance geographically distributed operations.

As understood by those of ordinary skill in the art, memory 506 of the server 502 optionally includes volatile and/or nonvolatile memory including, for example, RAM, ROM, and magnetic or optical disks, among others. It is also understood by those of ordinary skill in the art that although illustrated as a single server, the illustrated configuration of server 502 is given only by way of example and that other types of servers or computers configured according to various other methodologies or architectures can also be used. Server 502 shown schematically in FIG. 5, represents a server or server cluster or server farm and is not limited to any individual physical server. The server site can be deployed as a server farm or server cluster managed by a server hosting provider. The number of servers and their architecture and configuration can be increased based on usage, demand and capacity requirements for the system 500. As also understood by those of ordinary skill in the art, computer 514 in these aspects, for example, can be a laptop, desktop, tablet, personal digital assistant (PDA), cell phone, server, or other types of computers. As known and understood by those of ordinary skill in the art, network 512 can include an internet, intranet, a telecommunication network, an extranet, or world wide web of a plurality of computers/servers in communication with one or more other computers through a communication network, and/or portions of a local or other area network.

As further understood by those of ordinary skill in the art, exemplary program product or program product 508 is optionally in the form of microcode, programs, cloud computing format, routines, and/or symbolic languages that provide one or more sets of ordered operations that control the functioning of the hardware and direct its operation. Program product 508, according to an exemplary aspect, also need not reside in its entirety in volatile memory, but can be selectively loaded, as necessary, according to various methodologies as known and understood by those of ordinary skill in the art.

As further understood by those of ordinary skill in the art, the term "computer-readable medium" or "machine-readable medium" refers to any medium that participates in providing instructions to a processor for execution. To illustrate, the term "computer-readable medium" or "machine-readable medium" encompasses distribution media, cloud computing formats, intermediate storage media, execution memory of a computer, and any other medium or device capable of storing program product 508 implementing the functionality or processes of various aspects of the present disclosure, for example, for reading by a computer. A "computer-readable medium" or "machine-readable medium" can take many forms, including but not limited to, non-volatile media, volatile media, and transmission media. Non-volatile media includes, for example, optical or magnetic disks. Volatile media includes dynamic memory, such as the main memory of a given system. Transmission media includes coaxial cables, copper wire and fiber optics, including the wires that comprise a bus. Transmission media can also take the form of acoustic or light waves, such as those generated during radio wave and infrared data communications, among others. Exemplary forms of computer-readable media include a floppy disk, a flexible disk, hard disk, magnetic tape, a flash drive, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave, or any other medium from which a computer can read.

Program product 508 is optionally copied from the computer-readable medium to a hard disk or a similar intermediate storage medium. When program product 508, or portions thereof, are to be run, it is optionally loaded from their distribution medium, their intermediate storage medium, or the like into the execution memory of one or more computers, configuring the computer(s) to act in accordance with the functionality or method of various aspects. All such operations are well known to those of ordinary skill in the art of, for example, computer systems.

To further illustrate, in certain aspects, this application provides systems that include one or more processors, and one or more memory components in communication with the processor. The memory component typically includes one or more instructions that, when executed, cause the processor to provide information that causes at least one tendon damage model or component thereof, at least one guideline for tendon material repetitive stress or component thereof, and/or the like to be displayed (e.g., via computer 514 or the like) and/or receive information from other system components and/or from a system user (e.g., via computer 514 or the like).

In some aspects, program product 508 includes non-transitory computer-executable instructions which, when executed by electronic processor 504 perform at least: generating one or more S-N curves for one or more physical regimes of at least one tendon from one or more S-N curve data sets, wherein a given S-N curve comprises a plot of a magnitude of stress applied to the tendon versus a number of repetitions to failure of the tendon, and combining the S-N curves, or data derived therefrom, with one or more repetitive stress data sets to generate a tendon damage model.

System 500 also typically includes additional system components that are configured to perform various aspects of the methods described herein. In some of these aspects, one or more of these additional system components are positioned remote from and in communication with server 502 through electronic communication network 512, whereas in other aspects, one or more of these additional system components are positioned local, and in communication with server 502 (i.e., in the absence of electronic communication network 512) or directly with, for example, computer 514.

While the foregoing disclosure has been described in some detail by way of illustration and example for purposes of clarity and understanding, it will be clear to one of ordinary skill in the art from a reading of this disclosure that various changes in form and detail can be made without departing from the true scope of the disclosure and may be practiced within the scope of the appended claims. For example, all the methods, systems, and/or component parts or other aspects thereof can be used in various combinations. All patents, patent applications, websites, other publications or documents, and the like cited herein are incorporated by reference in their entirety for all purposes to the same extent as if each individual item were specifically and individually indicated to be so incorporated by reference.

What is claimed is:

1. A method of reducing the potential for repetitive stress injuries to human soft tissue in performing an assembly line manufacturing process, the method comprising:

obtaining at least one repetitive stress data set related to the soft tissue and to the assembly line manufacturing process, wherein the repetitive stress data set characterizes an exposure that a worker accrues in completing an assembly line task that forms part of the assembly line manufacturing process;

accessing at least information characterizing a first damage regime, wherein the first damage regime consists of a no damage regime, wherein the information quantifies a number of repetitions at a given stress for the soft tissue to transition out of the first damage regime;

predicting, based on at least the information and the repetitive stress data set, conditions sufficient for damage to the soft tissue, wherein the predicting comprises predicting conditions sufficient to transition from the first damage regime to a second damage regime, wherein the second damage regime consists of a sub-rupture damage regime;

determining, based on at least the predicting, at least one guideline for reducing a risk of a soft tissue material repetitive stress injury, wherein the at least one guideline specifies a limitation on a number of repetitions of a given movement of a supraspinatus tendon, wherein the at least one guideline is for reducing a risk of a supraspinatus tendon repetitive stress injury, wherein the determining comprises determining at least one guideline for reducing a risk of transitioning from the first damage regime to the second damage regime; and implementing the at least one guideline in the assembly line manufacturing process, wherein the implementing comprises modifying the assembly line task of the worker in conformance with the at least one guideline, and wherein the implementing comprises the worker performing the modified assembly line task in conformance with the at least one guideline.

2. The method of claim 1, wherein the repetitive stress data set comprises a force over a cross sectional area of the soft tissue and at least one of a number of repetitions for, or a duration of, at least one task of the process.

3. The method of claim 1, wherein the obtaining the at least one repetitive stress data set related to the soft tissue and to the process comprises estimating at least one stress distribution in the soft tissue.

4. The method of claim 1, wherein the accessing at least information characterizing a first damage regime comprises obtaining at least one of: ultrasound data, computerized axial tomography (CAT) scan data, magnetic resonance imaging (MRI) scan data, destructive testing data, cadaver material data, animal material data, polymer surrogate material data, molecular dynamic modeling (MDM) data, or publication data.

5. The method of claim 1, wherein the soft tissue further comprises a teres minor tendon, an infraspinatus tendon, a subscapularis tendon, a deltoid tendons, a biceps tendon, a triceps tendon, a brachioradialis tendon, a supinator tendon, a flexor carpi radialis tendon, a flexor carpi ulnaris tendon, an extensor carpi radialis tendon, an extensor carpi radialis brevis tendon, an iliopsoas tendon, an obturator internus tendon, an adductor longus tendon, an adductor brevis tendon, an adductor magnus tendon, a gluteus maximus tendon, a gluteus medius tendon, a quadriceps tendon, a patellar tendon, a hamstring tendon, a sartorius tendon, a gastrocnemius tendon, an Achilles tendon, a soleus tendon, a tibialis anterior tendon, a peroneus longus tendon, a flexor digitorum longus tendon, an interosseus tendon, a flexor digitorum profundus tendon, an abductor digiti minimi tendon, an opponens pollicis tendon, a flexor pollicis longus tendon, an extensor tendon, an abductor pollicis tendon, a flexor hallucis longus tendon, a flexor digitorum brevis tendon, a lumbrical tendon, an abductor hallucis tendon, a flexor digitorum longus tendon, an abductor digiti minimi tendon, an ocular tendon, a levator palpebrae tendon, a masseter tendon, a temporalis tendon, a trapezius tendon, a sternocleidomastoideon, a semispinalis capitis tendon, a splenius capitis tendon, a mylohyoid tendon, a thyrohyoid tendon, a sternohyoid tendon, a rectus abdominis tendon, an external oblique tendon, a transversus abdominis tendon, a latissimus dorsi tendon, or an erector spinae tendon.

6. The method of claim 1, further comprising individualizing the at least one guideline for a subject by applying one or more demographic variables for the subject to the at least one guideline.

7. The method of claim 1, further comprising:

obtaining one or more usage data sets for the soft tissue in a subject; and estimating damage to the soft tissue in the subject by comparing the usage data sets to the at least one guideline.

8. A computer system for reducing repetitive stress injuries to soft tissue in performing an assembly line manufacturing process, the system comprising at least one electronic processor that executes instructions to perform operations comprising:

obtaining at least one repetitive stress data set related to the soft tissue and to the assembly line manufacturing process, wherein the repetitive stress data set characterizes an exposure that a worker accrues in completing an assembly line task that forms part of the assembly line manufacturing process;

accessing at least information characterizing a first damage regime, wherein the first damage regime consists of a no damage regime, wherein the information quantifies a number of repetitions at a given stress for the soft tissue to transition out of the first damage regime;

predicting, based on at least the information and the repetitive stress data set, conditions sufficient for damage to the soft tissue, wherein the predicting comprises predicting conditions sufficient to transition from the first damage regime to a second damage regime, wherein the second damage regime consists of a sub-rupture damage regime; and determining, based on at least the predicting, at least one guideline for reducing a risk of a soft tissue material repetitive stress injury, wherein the at least one guideline specifies a limitation on a number of repetitions of a given movement of a supraspinatus tendon, wherein the at least one guideline is for reducing a risk of a supraspinatus tendon repetitive stress injury, wherein the determining comprises determining at least one guideline for reducing a risk of transitioning from the first damage regime to the second damage regime; whereby the at least one guideline is implemented in the assembly line manufacturing process, wherein the implementing comprises modifying the assembly line task of the worker in conformance with the at least one guideline, and wherein the guideline is implemented by the worker performing the modified assembly line task in conformance with the at least one guideline.

9. The system of claim 8, wherein the repetitive stress data set comprises a force over a cross sectional area of the soft tissue and at least one of a number of repetitions for, or a duration of, at least one task of the process.

10. The system of claim 8, wherein the obtaining the at least one repetitive stress data set related to the soft tissue and to the process comprises estimating at least one stress distribution in the soft tissue.

11. The system of claim 8, wherein the accessing at least information characterizing a first damage regime comprises obtaining at least one of: ultrasound data, computerized axial tomography (CAT) scan data, magnetic resonance imaging (MRI) scan data, destructive testing data, cadaver material data, animal material data, polymer surrogate material data, molecular dynamic modeling (MDM) data, or publication data.

12. The system of claim 8, wherein the soft tissue further comprises a teres minor tendon, an infraspinatus tendon, a subscapularis tendon, a deltoid tendons, a biceps tendon, a triceps tendon, a brachioradialis tendon, a supinator tendon, a flexor carpi radialis tendon, a flexor carpi ulnaris tendon, an extensor carpi radialis tendon, an extensor carpi radialis brevis tendon, an iliopsoas tendon, an obturator internus tendon, an adductor longus tendon, an adductor brevis tendon, an adductor magnus tendon, a gluteus maximus tendon, a gluteus medius tendon, a quadriceps tendon, a patellar tendon, a hamstring tendon, a sartorius tendon, a gastrocnemius tendon, an Achilles tendon, a soleus tendon, a tibialis anterior tendon, a peroneus longus tendon, a flexor digitorum longus tendon, an interosseus tendon, a flexor digitorum profundus tendon, an abductor digiti minimi tendon, an opponens pollicis tendon, a flexor pollicis longus tendon, an extensor tendon, an abductor pollicis tendon, a flexor hallucis longus tendon, a flexor digitorum brevis tendon, a lumbrical tendon, an abductor hallucis tendon, a flexor digitorum longus tendon, an abductor digiti minimi tendon, an ocular tendon, a levator palpebrae tendon, a masseter tendon, a temporalis tendon, a trapezius tendon, a sternocleidomastoideon, a semispinalis capitis tendon, a splenius capitis tendon, a mylohyoid tendon, a thyrohyoid tendon, a sternohyoid tendon, a rectus abdominis tendon, an external oblique tendon, a transversus abdominis tendon, a latissimus dorsi tendon, or an erector spinae tendon.

13. The system of claim 8, wherein the operations further comprise individualizing the at least one guideline for a subject by applying one or more demographic variables for the subject to the at least one guideline.

14. The system of claim 8, wherein the operations further comprise:

obtaining one or more usage data sets for the soft tissue in a subject; and estimating damage to the soft tissue in the subject by comparing the usage data sets to the at least one guideline.

15. A method of reducing the potential for repetitive stress injuries to human soft tissue in performing an assembly line manufacturing process, the method comprising:

obtaining at least one repetitive stress data set related to the soft tissue and to the assembly line manufacturing process, wherein the repetitive stress data set characterizes an exposure that a worker accrues in completing an assembly line task that forms part of the assembly line manufacturing process;

accessing at least information characterizing a first damage regime, wherein the first damage regime consists of a sub-rupture damage regime, wherein the information quantifies a number of repetitions at a given stress for the soft tissue to transition out of the first damage regime;

predicting, based on at least the information and the repetitive stress data set, conditions sufficient for damage to the soft tissue, wherein the predicting comprises predicting conditions sufficient to transition from the first damage regime to a second damage regime, wherein the second damage regime consists of a tear propagation regime;

determining, based on at least the predicting, at least one guideline for reducing a risk of a soft tissue material repetitive stress injury, wherein the at least one guideline specifies a limitation on a number of repetitions of a given movement of a supraspinatus tendon, wherein the at least one guideline is for reducing a risk of a supraspinatus tendon repetitive stress injury, wherein the determining comprises determining at least one guideline for reducing a risk of transitioning from the first damage regime to the second damage regime; and implementing the at least one guideline in the assembly line manufacturing process, wherein the implementing comprises modifying the assembly line task of the worker in conformance with the at least one guideline, and wherein the implementing comprises the worker performing the modified assembly line task in conformance with the at least one guideline.

16. The method of claim 15, wherein the accessing at least information characterizing a first damage regime comprises obtaining at least one of: ultrasound data, computerized axial tomography (CAT) scan data, magnetic resonance imaging (MRI) scan data, destructive testing data, cadaver material data, animal material data, polymer surrogate material data, molecular dynamic modeling (MDM) data, or publication data.

17. The method of claim 15, wherein the obtaining the at least one repetitive stress data set related to the soft tissue and to the process comprises estimating at least one stress distribution in the soft tissue.

18. A computer system for reducing repetitive stress injuries to soft tissue in performing an assembly line manufacturing process, the system comprising at least one electronic processor that executes instructions to perform operations comprising:

obtaining at least one repetitive stress data set related to the soft tissue and to the assembly line manufacturing process, wherein the repetitive stress data set characterizes an exposure that a worker accrues in completing an assembly line task that forms part of the assembly line manufacturing process;

accessing at least information characterizing a first damage regime, wherein the first damage regime consists of a sub-rupture damage regime, wherein the information quantifies a number of repetitions at a given stress for the soft tissue to transition out of the first damage regime;

predicting, based on at least the information and the repetitive stress data set, conditions sufficient for damage to the soft tissue, wherein the predicting comprises predicting conditions sufficient to transition from the first damage regime to a second damage regime, wherein the second damage regime consists of a tear propagation regime;

determining, based on at least the predicting, at least one guideline for reducing a risk of a soft tissue material repetitive stress injury, wherein the at least one guideline specifies a limitation on a number of repetitions of a given movement of a supraspinatus tendon, wherein the at least one guideline is for reducing a risk of a supraspinatus tendon repetitive stress injury, wherein the determining comprises determining at least one guideline for reducing a risk of transitioning from the first damage regime to the second damage regime; and implementing the at least one guideline in the assembly line manufacturing process, wherein the implementing comprises modifying the assembly line task of the worker in conformance with the at least one guideline, and wherein the implementing comprises the worker performing the modified assembly line task in conformance with the at least one guideline.

19. The system of claim 18, wherein the accessing at least information characterizing a first damage regime comprises obtaining at least one of: ultrasound data, computerized axial tomography (CAT) scan data, magnetic resonance imaging (MRI) scan data, destructive testing data, cadaver material data, animal material data, polymer surrogate material data, molecular dynamic modeling (MDM) data, or publication data.

* * * * *